United States Patent
Warner et al.

(10) Patent No.: US 7,550,136 B2
(45) Date of Patent: Jun. 23, 2009

(54) PHOTO-REACTIVE POLYMERS AND DEVICES FOR USE IN HAIR TREATMENTS

(75) Inventors: John C. Warner, Quincy, MA (US); Amy S. Cannon, Jamaica Plain, MA (US); Jennifer Raudys, Brockton, MA (US); Arundhati Undurti, Walpole, MA (US)

(73) Assignee: University of Massachusetts, Boston, MA (US)

( * ) Notice: Subject to any disclaimer, the term of this patent is extended or adjusted under 35 U.S.C. 154(b) by 692 days.

(21) Appl. No.: 10/742,315

(22) Filed: Dec. 19, 2003

(65) Prior Publication Data

US 2004/0206368 A1 Oct. 21, 2004

Related U.S. Application Data

(60) Provisional application No. 60/435,959, filed on Dec. 20, 2002.

(51) Int. Cl.
*A61Q 5/04* (2006.01)
(52) U.S. Cl. .................... 424/70.2; 424/70.11; 132/210
(58) Field of Classification Search ................. None
See application file for complete search history.

(56) References Cited

U.S. PATENT DOCUMENTS

| | | | |
|---|---|---|---|
| 5,118,495 A | | 6/1992 | Nafziger et al. |
| 5,300,285 A | * | 4/1994 | Halloran et al. ............ 424/70.2 |
| 5,884,635 A | | 3/1999 | O'Brien et al. |
| 5,911,979 A | | 6/1999 | Midha et al. |
| 6,363,215 B1 | | 3/2002 | Cafaro |
| 2001/0013513 A1 | | 8/2001 | Chan |
| 2003/0091602 A1 | * | 5/2003 | Witteler et al. .............. 424/401 |

OTHER PUBLICATIONS

International Search Report mailed Sep. 24, 2004.
Cunningham, "Design of Functional Polymeric Microspheres for Bioseparations", http://www.chemeng.queensu.ca/People/Personal/Webs/mfc/Mike2%20-%20Publication%20and%20Awards.htm, Mar. 19, 2004.
European Search Report for PCT/US0341349, issued Jan. 21, 2009.

* cited by examiner

*Primary Examiner*—Jyothsna A Venkat
(74) *Attorney, Agent, or Firm*—Fish & Richardson P.C.

(57) ABSTRACT

The invention provides new methods to treat hair to achieve a permanent wave, curl, or straightness.

16 Claims, 1 Drawing Sheet

PHOTO-REACTIVE POLYMERS AND DEVICES FOR USE IN HAIR TREATMENTS

CROSS REFERENCE TO RELATED APPLICATIONS

This application claims the benefit from U.S. Provisional Patent Application No. 60/435,959, filed on Dec. 20, 2002, the entire contents of which is hereby incorporated by reference herein.

TECHNICAL FIELD

This invention relates to hair treatments and devices.

BACKGROUND

The process of curling or straightening hair, getting a "perm," can be time consuming and typically involves the use of harsh chemicals that can be hazardous to human health and to the environment. Many of these processes use chemical reduction and subsequent oxidation of disulfide bonds within hair protein to maintain induced physical properties, such as a curling or straightening of the hair.

SUMMARY

The invention is based on the discovery that certain water-soluble, photoreactive polymers can be used in simple and convenient methods of treating hair to provide a permanent, yet reversible, stiffening of the hair shafts, to achieve a permanent wave, curl, or straightness, of the hair.

In general, the invention features methods of treating hair to induce a permanent, reversible stiffening of hair shafts by optionally wetting the hair; applying a water-soluble photoreactive polymer, e.g., including photoreactive moieties, to the hair, in which the photoreactive polymer includes at least portions derived from a photoreactive monomer and a water-soluble monomer; shaping the hair into a desired configuration; and irradiating the polymer at a wavelength and for a sufficient time to render the polymer water insoluble thereby stiffening the hair shafts sufficiently to maintain the desired configuration. For example, the hair shafts can be shaped into a wave, a straight configuration, or a curled configuration.

In these methods, the polymer can be irradiated at a wavelength and for a time sufficient to crosslink the polymer. Once the perm is to be removed, this can be easily done by removing the crosslinks in the polymer to remove the desired configuration.

In another aspect, the invention features a hair curler that includes a transparent cylinder that emits radiation. The hair curler can further include a cylindrical cover that snaps over the cylinder after hair is wrapped around the cylinder to hold the hair in place. The new hair curlers can emit chemiluminescent or phosphorescent radiation, or can include light bulbs or LEDs that are powered by electricity.

The invention also features a hair curling device that includes a handle; a cylindrical core attached to the handle that emits radiation; and an elongate cover that fits over the core and is designed to hold hair against the core when the hair is wrapped around the core or pulled between the core and the cover.

In another aspect, the invention includes a hair straightening device that includes an elongated transparent plate that emits radiation; a handle attached to the flat portion; and a flat cover designed to hold hair against the elongated flat portion when the hair is inserted and pulled between the flat portion and flat cover. Both of these devices can be designed to emit UV radiation.

In another aspect, the invention features a method of toning hair that includes applying a water-soluble photoreactive polymer to the hair, where the photoreactive polymer includes at least portions that are derived from a photoreactive monomer and a water-soluble monomer; irradiating the polymer at a wavelength and for a sufficient time to render the polymer water insoluble; and applying a toning agent to the hair. The toning agent can include a dye. The method can further include removing the polymer to remove the toning agent.

In another aspect, the invention features a kit for treating hair that includes a water-soluble photoreactive polymer, where the photoreactive polymer comprises at least portions that are derived from a photoreactive monomer and a water-soluble monomer, and instructions for use of the polymer to treat hair according to any of the methods described herein. The kit can further include a toning agent and instructions for toning hair. The hair can be treated to induce a permanent, reversible stiffening of hair shafts. The kit can further include an agent for removing the polymer, e.g., a photolyase.

Other aspects or embodiments may include combinations of the features in the aspects above and/or one or more of the following. The portions are substantially the entire photoreactive polymer. The hair shafts are shaped into a wave. The hair shafts are shaped into a straight configuration. The hair shafts are shaped into a curled configuration. The polymer is irradiated at a wavelength, and for a time sufficient to crosslink the polymer. The wavelength is from about 200 nm to about 600 nm. The wavelength is from about 250 nm to about 400 nm. The method further includes removing the crosslinks in the polymer to remove the desired configuration. The removing is done with a photolyase. The photoreactive monomers are, for example, vinylbenzylthymines, vinylbenzyluracils, vinylphenylcinnamates, vinylcoumarins, vinylchalcones, N-acryloylamidopyridinium halides, or mixtures thereof. The photoreactive monomer comprises from about 3% to about 50% by weight of the polymer. The photoreactive monomer includes from about 10% to about 25% by weight of the polymer. The method includes employing a photosensitizer. The photosensitizers are, for example, benzoporphyrins, benzophenones, cinnamates, Methylene Blues, fluoresceins, or mixtures thereof. The water-soluble monomer is an ionic moiety. The water-soluble monomer is non-ionic, and includes a group capable of hydrogen bonding. The water-soluble monomers are, for example, vinylbenzylammonium cations, vinylbenzylsulfonium cations, N-alkylvinylpyridinium ions, vinylphenylsufonate anions, vinylbenzoate anions, vinyphenylphosphate anions, vinylbenzamide ions, vinylphenylsufonamide ions, ethylene oxides, propylene oxides, oxazolines, or mixtures thereof. The hair curler further includes a cylindrical cover that snaps over the cylinder after hair is wrapped around the cylinder to hold the hair in place. The hair curler emits radiation that is chemiluminescent or phosphorescent.

A "permanent, reversible" wave, curl, or straightness of hair, means that each hair shaft is stiffened, and thus maintains whatever wave, curl, or straightness has been induced, for a set period of time, or until the hair is specifically treated to remove the perm. If no treatment to remove the permanent wave is applied within the set period of time, exposure of the hair to repeated washings may also cause the perm to be relaxed or removed, thereby allowing the hair to assume its natural state, much like a normal chemical perm. The unique advantage of the new methods is that the perm can be reversed at will and at any time.

"Derived from" as used herein means made from the associated monomers by polymerization, made from the associated monomers by grafting, and/or made from synthetic modification of such moieties.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and are not intended to be limiting.

The new methods and devices for treating hair are non-toxic and eliminate hazardous processes typically used to achieve a permanent wave in hair. Compared to known chemical "perm" solutions, the new methods and compositions require only one solution, significantly reduce processing time, can be used easily at home, provide a simple reversal of the "perm" at any time by applying a second non-toxic solution, are less damaging to hair, and require no waiting or setting time.

The details of one or more embodiments of the invention are set forth in the accompanying drawings and the description below. Other features, objects, and advantages of the invention will be apparent from the description and drawings, and from the claims.

DETAILED DESCRIPTION

General Methodology

Figures 1A, 1B:
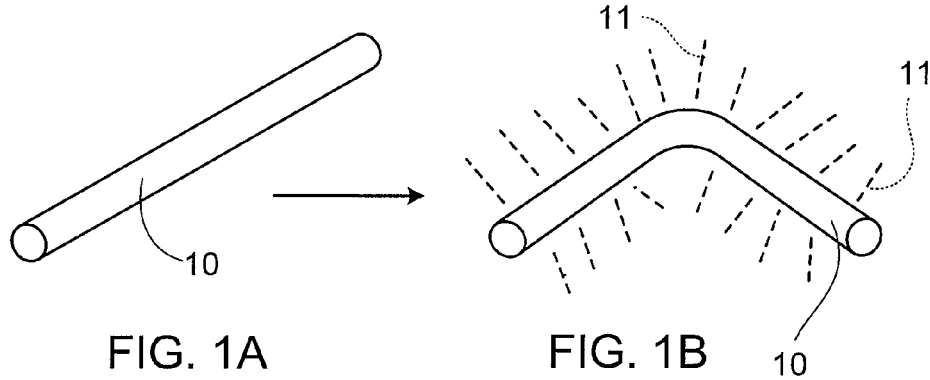
FIGS. 1A and 1B are schematic diagrams of a light-emitting cylindrical device that forms the core of a new light-emitting hair curler.

The new methods are simple, and use a single solution. The general steps are: wetting the hair, applying a polymer to the hair, shaping the hair into a desired configuration, and setting the polymer to stiffen the hair shafts sufficiently to maintain the desired configuration. The desired configuration can be, for example, a loose or tight curl, a gentle wave, or a straightening of the hair. The polymers are water-soluble, photoreactive polymers, such as water-soluble photoresists (WSPR), and are made water-insoluble and stiffer by irradiation with an appropriate light, e.g., by crosslinking of the WSPR. This stiffening, e.g., crosslinking, of the polymers on the surface of the hair shafts causes the hair shafts to stiffen as well, thereby enabling them to maintain a desired configuration.

The perm can be removed at will, by applying a second solution to the hair that removes the crosslinks from the polymers, thereby causing them to become water-soluble, which allows them to be washed out of the hair Photoreactive Polymers The polymers used for the new methods are any polymers that include portions that are derived from a photoreactive monomer and a water-soluble monomer. The water-soluble monomers are, for example, cationic or anionic monomers, or they can contain an appropriate ratio of oxygen and nitrogen to carbon so as to promote hydration through hydrogen bonding. Examples of useful water-soluble monomers are vinylbenzylammonium cations, vinylbenzylsulfonium cations, N-alkylvinylpyridinium ions, vinylphenylsufonate anions, vinylbenzoate anions, vinyphenylphosphate anions, vinylbenzamide ions, and vinylphenylsufonamide ions. Suitable non-ionic monomers include, for example, ethylene oxide, propylene oxide and oxazolines, for example, 2-ethyl-2-oxazoline.

Suitable photoreactive monomers must be capable of polymerization with the solubilizing monomer. They must also induce a solubility or polarity change within the molecule upon irradiation so as to impart a macroscopic change in the bulk polymer. Useful examples include vinylbenzylthymine, vinylbenzyluracil, vinylphenylcinnamate, vinylcoumarins, vinylchalcones, and N-acryloylamidopyridinium halides.

Upon irradiation with an appropriate radiation, e.g., light such as ultraviolet (UV) light, these photoreactive polymers are activated, e.g., crosslinked or otherwise stiffened, to become water-insoluble.

Specific polymers that can be used for this application are polymers, such as polystyrene polymers, with hydrating moieties and pendant photoreactive moieties that upon irradiation undergo a crosslinking reactions, for example, [2+2] photo-dimerization (cyclization) reactions. Examples of the photoreactive moieties include thymine (e.g., benzyl thymine), uracil, and other organic molecules capable of participating in [2+2] cyclization reactions in polymer chains. Such polymers can include multi-functional vinylbenzyl and vinylphenyl pendant thymine (and/or uracil) groups, and are described, for example, in U.S. Pat. Nos. 5,708,106 and 5,455,349. Other examples include, but are not limited to, polymers containing cinnamates (Nakayama et al., Polymer Sci., Part A: Polymer Chemistry (1992), 30(11):2451-7), coumarins (Delzenne et al., Ind. Chim. Belge (1967), 32(Spec. No.), 373-8), and chalcones (Mihara et al., Polymer Journal (Tokyo, Japan) (2002), 34(5), 347-355). Other useful polymers include those described in "New Thymine and Uracil Photo-polymers" Cheng et al., Proceedings of the IS&T's 47th Annual Conference. The Physics and Chemistry of Imaging Systems, 810, 1994; "Copolymeric Mordants and Photographic Products and Processes Containing Same," Grasshoff et al., U.S. Pat. No. 5,395,731 (Mar. 7, 1995); "Vinylbenzyl Thymine Monomers and Their Use in Photoresists," Grasshoff et al., U.S. Pat. No. 5,455,349 (Oct. 3, 1995); "The Synthesis of 1-[Vinylbenzyl]thymine, A Very Versatile Monomer," Cheng et al., J. Polymer Sci., Part A: Polymer Chem. 1995, 33, 2515; "Method of Imaging Using a Polymeric Photoresist Having Pendant Vinylbenzyl Thymine Groups," Grasshoff et al., U.S. Pat. No. 5,616,451 (Apr. 1, 1997), and "Copolymers Having Pendant Functional Thymine Groups," Grasshoff et al., U.S. Pat. No. 5,708,106 (Jan. 13, 1998). Many such monomers, and polymers made from such monomers, are commercially available.

Another photo-activation mechanism that can be used to render a photoreactive polymer water-insoluble is a photo ring expansion process that involves pyridinium ylides (Streith, Chimia (1991) 45(3):65-76). In general, any photo-reaction that generates covalent bonds, or dramatically alters molecular polarity and renders the polymer water-insoluble will be useful in this process.

The photoreactive moieties of the polymer include about 3%-50% by weight of the polymer, e.g., 4, 5, 7, 10, 12, 15, 20, 25, 30, 35, 40, or 45% by weight.

Once applied to hair, and the hair has been set into its desired configuration, the water-soluble polymers are irradiated for a time sufficient to crosslink or otherwise activate the polymer and render it water-insoluble. Broad UV light or actinic radiation, e.g., UV light at specific wavelengths, such as 285 nm, can be used to cause crosslinking of the polymer. Irradiation of the polymer initiates, for example, [2+2] cyclization reactions between the photoreactive moieties, which causes the polymer to become water-insoluble and stick to the hair, as well as to become stable to other environmental conditions (e.g., air and light). Nevertheless, the polymer coating on each hair shaft does not impair the overall feel of the hair.

The specific polymers listed above that are based on thymine as the photoreactive moieties are activated or crosslinked by light at a wavelength of about 285 nm. Other polymer systems are responsive to light irradiation at a wavelength of up to about 360 nm. In addition, the effective wavelength of light can be adjusted by adding a photosensitizing comonomer, e.g., by incorporating a sensitizer into the polymer backbone, or by adding a sensitizer to the application solution. Both of these methods will allow a molecule of one wavelength to, by energy transfer, sensitize the photoreaction to a desired wavelength. Suitable photosensitizers that can be added to the solution include benzoporphyrin, benzophenones, cinnamates, Methylene Blue, and fluorescein.

Other polymers that can be used can be derived from vinylbenzylthymine [VBT] and triethylammoniumvinylbenzylbromide [TEQ] in ratios of 1:4 and 1:8, respectively. The details of the synthesis of these polymers are described in the Examples below. In addition, other photopolymer systems based on cinnamic acid derivatives also work in the new methods.

Heat, for example, applied from a hair dryer, can aid in the cross-linking of the photoreactive polymers. Water-soluble additives, for example, water soluble azo initiators, can also be used to aid in the cross-linking of the photoreactive polymers. Azo initiators can be selected with the appropriate temperature half-life, typically the 10 hour half-life decomposition temperature T. Examples of water-soluble azo initiators include 2,2'-Azobis[2-(5-methyl-2-imidazolin-2-yl)propane]dihydrochloride (T=41° C.), 2,2'-Azobis[N-(2-carboxyethyl)-2-methylpropionamidine]tetrahydrate (T=57° C.), and 2,2'-Azobis[2-methyl-N-(2-hydroxyethyl)propionamide] (T=86° C.). Water-soluble azo initiators are available from Wako Chemicals USA, Richmond, Va.

The length of time that the polymers maintain the "shape" of the hair is controlled by the identity of the polymer (specifically the monomer composition from which the polymer is derived). In other word, one can control the length of time that the "perm" will last by adjusting one or more of the following: (1) the ratio of photo-reactive monomer to solubilizing monomer incorporated into the polymer can be increased (while these results will vary depending on many parameters, a 1:1 polymer ratio should provide the longest lasting perm, a 1:2 ratio will be shorter, a 1:4 ratio will be shorter lasting, a 1:8 ratio shorter still, and a 1:16 will be very short lived); (2) the length of time that the polymer is irradiated can be varied (in general, the longer the irradiation time, the greater the crosslink density, and the longer "hold" of the polymer); and (3) the identity of the photoreactive monomer can be changed. This will provide many gradations of "photoactivity." For example, photoreactive polymers based on thymine are more sensitive than those based on cinnamates, thus given the same amount of irradiation, the thymine-based polymers will provide a longer lasting perm than the cinnamates-based polymers.

Sources of Irradiation

Light irradiation can be applied to the treated hair by using a conventional UV lamp as found in tanning salons, or special lamps. For example, one can use typical mineral lamp thin layer chromatography irradiators (e.g., Mineralight®—Model UVGL-25, VVP, Inc.) In the home, one can use a typical "black light." Any source of ultraviolet light can be used. Of course, photopolymers can be chosen that have extended activity into longer wavelengths up to about 360 nm or more. In these cases, a longer wavelength light source is used, for example, a visible wavelength light source, such as a standard incandescent bulb.

The treated hair can be irradiated from the "outside," e.g., with a lamp, or from "within" a curl of hair, by using a "curler" that includes a light source inside. For example, a hair "curler" can be made that projects light from a transparent cylinder. This would allow irradiation of the hair strands directly from "within" a curl. The hair can be irradiated from within through a UV transparent cylinder with an appropriate light source. This would allow strands of hair on the "inside" or concave side of the curl to be processed. Light could also be applied from an external source so as to allow strands of hair on the "outside" or convex side of the curl to be processed. In some applications, it may be desirable to combine both methods of irradiation.

FIG. 1A shows a transparent plastic cylinder 10 that contains one or more chemicals that emit the proper irradiation (e.g., it generates the appropriate amount and wavelength of irradiation) to photo-activate one of the polymers described herein. The device can be a single-use, disposable plastic cylinder that contains two components separated by a wall or membrane. As shown in FIG. 1B, when the cylinder is twisted or squeezed, the internal wall or membrane is broken to allow the two components, e.g., chemical solutions, to mix, creating chemiluminescence (shown as irradiation 11).

Figures 2A, 2B, 2C:
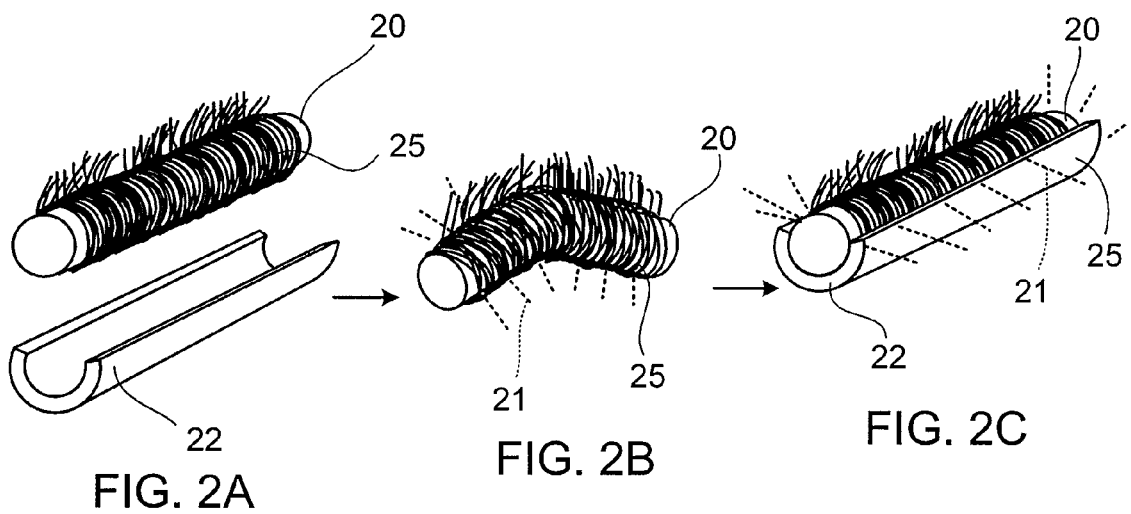
FIGS. 2A to 2C are schematic diagrams of a light-emitting hair curler in use.

FIGS. 2A to 2C show the use of a new light-emitting hair curler. As shown in FIG. 2A, the hair 25 is wrapped around an inexpensive, disposable plastic cylinder 20 that contains two components separated by a wall or membrane (not shown). When the cylinder is twisted or squeezed, the internal wall or membrane is broken to allow the two components, e.g., chemical solutions, to mix, creating chemiluminescence 21, providing light of the appropriate wavelength. The polymer and the nature of the light would be matched to effect the photo-crosslinking reaction and provides a simple "do-it-yourself at-home" process. The hair is held in place on the cylinder 20 by a cover 22, which can be made of plastic, and be in the shape of a cut open cylinder that is of the right size to hold the hair wrapped around the cylindrical core in place. To permit external irradiation using a UV lamp (in addition to the internal irradiation emitted from the central cylinder), the cover 22 can be transparent to the appropriate UV light or contain cutouts or openings to permit light to contact the hair wrapped around the central cylinder. Thus, the user has the option of applying internal irradiation from cylinder 20, applying external irradiation through cover 22 (e.g., if the central cylinder does not generate its own light, e.g., if it is merely solid or hollow plastic), or both.

The chemically powered lights in the central transparent cylinder can be either "single use" lights when using a photochromic material (e.g., Luminol® as described in McCapra, "The chemiluminescence of organic compounds," Q. Rev., Chem. Soc. (1966), 20(4):485-510) or "multi-use"

lights when using a phosphorescent material (e.g., zinc sulfide, as described in Alfrey, G. F. "Luminescence of zinc sulfide and cadmium sulfide," Proc. Int. Conf. Lumin. (1968), Meeting Date 1966, 1040-3). These multi-use light cylinders can be "recharged" by holding them under a light source for a set period of time, and then curling the hair around the cylinders.

In other embodiments, the central cylinder can include a standard light source rather than a chemical light source. For example, the transparent cylinder can house a set of electrically powered lights (e.g., LEDS or conventional bulbs) powered by batteries or connected to a power supply through one or more wires that run from inside the cylinder to one power cord that exists the cylinder. Multiple cylinders can be connected to a single power cord, and the entire system is grounded to avoid electric shock.

Figure 3:
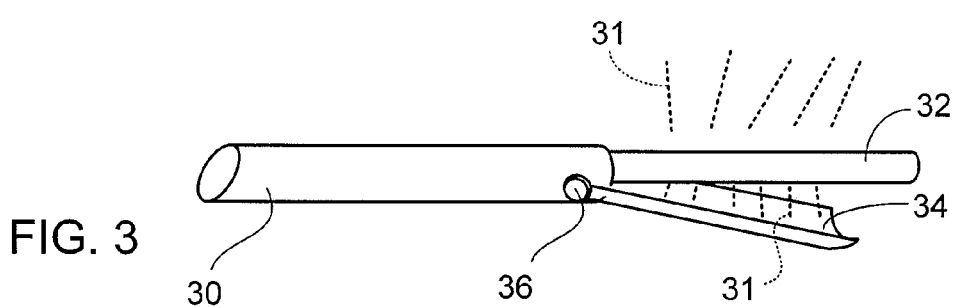
FIG. 3 is a schematic diagram of a light-emitting hair curling device.

Hair can also be set into a desired configuration by using a light-emitting hair curling device or a light-emitting hair straightening device. For example, FIG. 3 shows, in schematic form, a hair curling device that looks much like a standard "curling iron," except that the central cylinder is transparent to transmit or emit irradiation at a proper wavelength to photo-active one of the polymers described herein. The light-emitting hair curling device includes a handle 30, a transparent cylinder 32 that transmits or emits radiation 31, and an elongated member 34 that holds the hair against the cylinder 32.

In use, a length of hair is placed between the cylinder 32 and the elongate member 34, and the member 34 is pivoted about pivot point or hinge 36 to clamp the hair against the cylinder 32. The hair can be curled around the cylinder, or merely pulled over the cylinder to impart a partial curl or wave. The central cylinder can be passive, i.e., by merely transmitting light from a UV lamp or other external source, or it can be active, i.e., by having an internal light source that is emitted from all sides of the cylinder 32. The elongate member 34 can be transparent to permit external irradiation as required.

The central cylinder 32 can also be heated to provide a drying effect on the hair. Means other than elongate member 34 can be used to temporarily secure the hair around the cylinder 32. The central cylinder 32 can be a replaceable chemiluminescent device or can be powered by electricity (e.g., by batteries in handle 30, or by a power cord, not shown) and contain standard light bulbs or LEDs.

Figure 4:
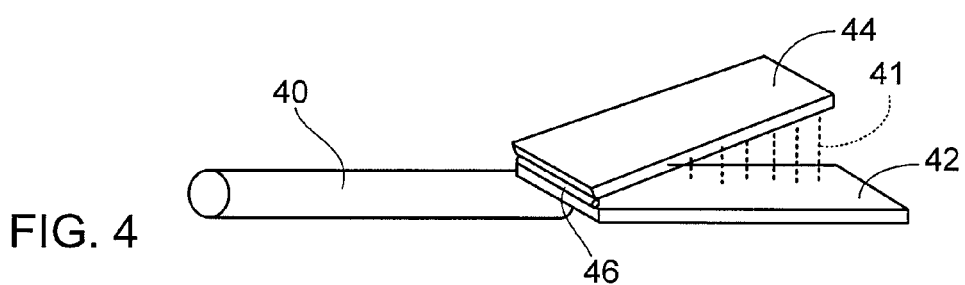
FIG. 4 is a schematic diagram of a light-emitting hair straightening device.

FIG. 4 illustrates a similar device used for straightening hair. This device includes a handle 40 and a flat transparent plate 42. This plate can be passive and merely transmit light of the proper radiation generated by a UV lamp or other light source, or active and generate and emit light 41 from inside the plate 42 as described herein for the light-emitting hair curler. Hair is held against the plate by an elongate cover plate 44 that can be moved about pivot or hinge 46. In use, hair is placed between the plates 42 and 44, and is clamped in place as the hair is pulled from between the plates. Either the plate 42 emits light 41 or transmits light from an external source. Alternatively, or in addition, irradiation can pass through cover plate 44 if it is transparent to the proper wavelength of irradiation.

The transparent plate 42 can also be heated to provide a drying effect on the hair. Means other than elongate cover plate 44 can be used to temporarily clamp the hair against plate 42. The plate 42 can be a replaceable chemiluminescent device or can be powered by electricity (e.g., by batteries in handle 40, or by a power cord, not shown) and contain standard light bulbs or LEDs.

Removing the Perm

The perm can be immediately reversed at any time by applying a specific wash solution. To relax the perm, the polymers coating the hair must be treated to remove the crosslinking. For example, the polymer-coated hair can be contacted with an enzyme that recognizes, for example, [2+2] cyclization polymers, forming a polymer-enzyme mixture on the hair. The mixture on the hair is then irradiated, e.g., with ambient light (e.g., yellow or any visible light) in the shower or bathroom, for a time sufficient to degrade the crosslinks, e.g., on the order of a few seconds or minutes, thus solubilizing the polymer.

The enzyme that recognizes the [2+2] cyclization polymers can be a photolyase, such as DNA and other photolyases from various bacteria (such as E. coli, in which DNA photolyase is encoded by the phr gene) and other organisms (e.g., fish and frogs). Only catalytic amounts of the enzyme are required (e.g., 0.1% to 1% by weight) in the wash solution.

Dying Permed Hair

The treated hair also can be "dyed" with a toning agent. This coloration can be maintained or removed at will by applying and removing the polymer as described herein. This method allows for the application of a colorant in hair that does not actually interact at the molecular level with the hair, but is bound to the immobilized polymer, which is, in turn, bound to the hair. This provides a reversible process whose duration of application can be controlled by removing the polymer at will. There are several FD&C approved dyes that can be used in this new method. If the dyes are non-toxic anionic colorants, they can be used with cationic photoreactive polymers. Alternatively, if the colorant is cationic, it can be used with an anionic photoreactive polymer.

Applying a solution of these dyes to treated hair allows for the "toning" of the hair by immobilized electrostatic attraction of a cationic polymer to an anionic dye. As in the perming method, to make the polymer initially soluble, the photoreactive monomer is copolymerized with a water-soluble monomer. These polymers are usually ionic, either cationic (bearing a positive charge) or anionic (bearing a negative charge). Once the photoreactive polymers are set on the hair, e.g., by crosslinking, and have become water-insoluble, the treated hair can then be dyed. When presented with an aqueous solution of a dye of opposite charge, the dye will "stick" via electrostatic forces to the polymer.

A typical procedure is as follows: A 5% aqueous dye solution is prepared using an FD&C dye. Hair treated with one of the photoreactive polymers described herein (and the appropriate irradiation) is washed, and is then "wiped" with a towel-applicator that has been submerged in the dye solution. The hair is allowed to stand with the solution for 5 minutes and then any remaining dye that has not bonded to the polymer coating on the hair shafts is removed by rinsing. Alternatively, the dye can be applied in a gel or other standard carrier and massaged into the hair with gloved finger tips. Again, excess dye is rinsed out. The polymer treatment can be used to perm the hair before the dye is applied, or the hair can be dried normally if no shaping of the hair is desired before adding the dye. Alternatively, the dye can be bound to, for example, covalently bound, the photoreactive polymer and applied in one step, as long as the dye does not interfere with the photo-activation of the polymer.

The dye can be removed by applying a photolyase wash solution as described herein. When the polymer is removed, the dye comes out with it as well. Thus, the dye can be removed at will, without the need to wait for the hair to grow and be cut, or the need to use another dye to cover the original dye.

EXAMPLES

The invention is further described in the following examples, which do not limit the scope of the invention described in the claims.

Example 1

Synthesis of Triethylammoniumvinylbenzylbromide (TEQ)

10 ml of vinylbenzyl chloride and 9.9 ml of triethylamine were added to a round bottom flask, along with ~70 ml of isopropanol. The mixture was stirred for 24 hours. The solution was then cooled in an ice bath and white crystals formed in the liquid. The crystals were collected and washed with cold isopropanol. The filtrate was saved and crystals formed within the filtrate after some time. The solution was again cooled and the crystals were collected. This was repeated until no further crystals were afforded from the solution. The crystals were dried in a vacuum oven.

Example 2

Synthesis of Vinylbenzylthymine in a (VBT)1:(TEQ)4 Ratio 2 grams of vinyl benzyl thymine (VBT) and 8.364 grams of TEQ were measured into a round bottom flask. 40 ml of isopropanol were added. The solution was stirred and heated to 65° C. Once at 65° C., 0.1 gram of 2,2'-Azobis(2-methylpropionitrile) (AIBN) was added to the flask. The solution was held at 65° C. and stirred for 24 hours. The solution was cooled to room temperature, then rotary evaporated to concentrate the solution. The concentrated solution was then cooled to room temperature, then poured into ~200 ml of acetone (while stirring). A white powdery solid crashed out of the acetone/isopropanol mix. The powder was allowed to stir in the acetone, then filtered and washed with acetone.

Example 3

Synthesis of (VBT)1:(TEQ)8

1 gram of vinyl benzyl thymine (VBT) and 8.364 grams of TEQ were measured into a round bottom flask. 40 ml of isopropanol were added. The solution was stirred and heated to 65° C. Once at 65° C., 0.1 gram of 2,2'-Azobis(2-methylpropionitrile) (AIBN) was added to the flask. The solution was held at 65° C. and stirred for 24 hours. The solution was cooled to room temperature, then rotary evaporated to concentrate the solution. The concentrated solution was then cooled to room temperature, then poured into ~200 ml of acetone (while stirring). A white powdery solid crashed out of the acetone/isopropanol mix. The powder was allowed to stir in the acetone, then filtered and washed with acetone.

Example 4

Permanent Curl in Hair

With a Pasture pipette a 20% (1:4 VBT/TEQ)/(water) solution was applied to an 4.5" inch strand of hair approximately ¼" thick. The strand of hair was wrapped around a 1 cm diameter wire rod. The wet hair was allowed to rest undisturbed for five minutes, and was still slightly damp. The hair was then irradiated (under proper protection, e.g., by covering the face and neck with a cloth to block UV light from hitting the skin) under a short wave (254 nm) UV lamp for 10 minutes on one side. The strands of hair were unwrapped from the wire rod. The hair maintained the curl and was dry.

The treated hair was then washed with water for 30 seconds and vigorously agitated by running fingers through the hair. The strands of hair were then blow-dried completely. Once the strand of hair was dried, it maintained its curl. The curl was maintained over three shampooings over two days.

As a control, a sample of hair was treated under the same conditions as above with water instead of the polymer solution. The hair did not maintain its curl.

Example 5

Permanent Curl in Hair

With a Pasture pipette a 10% (1:8 VBT/TEQ)/(water) solution was applied to a 9" inch strand of hair approximately ½" thick. The strand of hair was wrapped around a 1 cm diameter metal rod. The damp hair was allowed to rest undisturbed for five minutes. The hair was then irradiated hair (under proper protection) under a short wave (254 nm) UV lamp for 15 minutes on each side of the rod. The strand of hair was unwrapped from the metal rod. The hair maintained the curl and was dry.

The strands of hair were then washed with tap water for 30 seconds. The strands of hair were left to air dry completely. Once the hair was dry, it maintained its curl better than the control, which was the treatment of strands of hair in an identical fashion with pure water instead of the polymer.

Example 6

Permanent Straightening of Hair

With a Pasture pipette a 10% (1:8 VBT/TEQ)/(water) solution is applied to a 9" inch strand of curled hair approximately ½" thick. The strand of hair is "pulled" to straighten it, and pressed between a piece of wood with a flat planar surface and a piece of quartz glass. The hair is then irradiated (under proper protection) through the quartz glass under a short wave (270 nm) UV lamp for 10 minutes. The strand of hair is removed, and maintains its straightness.

The strands of hair are then washed with tap water for 30 seconds. The strands of hair are left to air dry completely. Once the hair was dry, it maintained its straightness.

Example 8

Reversing the Perm

To a portion of processed hair, a 10 ml solution of Photolyase [1% in any appropriate buffer solution] is applied. The solution-treated hair is allowed to stand for 5 minutes in ambient room light. Upon rinsing the hair will return to its unprocessed condition.

Example 9

Dying the Hair

A portion of hair processed as described in EXAMPLE 4 is dampened with water. A 5% solution of FD&C BLUE #2 is applied to the hair with a dampened towel. The hair is allowed to stand with the dye in contact for 5 minutes. Upon rinsing with water, the dye sticks to the polymer coating the treated hair.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating hair to induce a permanent, reversible stiffening of hair shafts, the method comprising
    applying a water-soluble photoreactive polymer to the hair, wherein the photoreactive polymer comprises
        a photoreactive monomer selected from the group consisting of vinylbenzylthymines, vinylbenzyluracils, vinylphenylcinnamates, vinylcoumarins, vinylchalcones, N-acryloylamidopyridinium halides, and mixtures thereof and
        a water-soluble monomer selected from the group consisting of vinylbenzylammonium cations, vinylbenzylsulfonium cations, N-alkylvinylpyridinium ions, vinylphenylsufonate anions, vinylbenzoate anions, vinyphenylphosphate anions, vinylbenzamide ions, vinylphenylsufonamide ions, ethylene oxides, propylene oxides, oxazolines, and mixtures thereof;
    shaping the hair into a desired configuration; and
    irradiating the polymer at a wavelength from about 200 nm to about 600 nm to crosslink the polymer thereby stiffening the hair shafts sufficiently to maintain the desired configuration.

2. The method of claim 1, further comprising wetting the hair.

3. The method of claim 1, wherein the hair shafts are shaped into a wave.

4. The method of claim 1, wherein the hair shafts are shaped into a straight configuration.

5. The method of claim 1, wherein the hair shafts are shaped into a curled configuration.

6. The method of claim 1, wherein the wavelength is from about 250 nm to about 400 nm.

7. The method of claim 1, further comprising removing the polymer to remove the desired configuration.

8. The method of claim 1, wherein the polymer is removed by removing crosslinks in the polymer.

9. The method of claim 8, wherein the removing is done with a photolyase.

10. The method of claim 1, wherein photoreactive monomer comprises from about 3% to about 50% by weight of the polymer.

11. The method of claim 1, wherein the photoreactive monomer comprises from about 10% to about 25% by weight of the polymer.

12. The method of claim 1, including employing a photosensitizer.

13. The method of claim 12, wherein the photosensitizer is selected from the group consisting of benzoporphyrins, benzophenones, cinnamates, Methylene Blues, fluoresceins, and mixtures thereof.

14. A method of treating hair to induce a permanent, reversible stiffening of hair shafts, the method comprising
    applying a water-soluble photoreactive polymer to the hair, wherein the photoreactive polymer is formed from vinylbenzylthymine monomers and water-soluble trimethyl ammonium benzyl bromide monomers;
    shaping the hair into a desired configuration; and
    irradiating the polymer at a wavelength from about 200 nm to about 600 nm to crosslink the polymer thereby stiffening the hair shafts sufficiently to maintain the desired configuration.

15. The method of claim 14, further including employing a photosensitizer.

16. The method of claim 15, wherein the photosensitizer is selected from the group consisting of benzoporphyrins, benzophenones, cinnamates, Methylene Blues, fluoresceins, and mixtures thereof.

* * * * *